(12) United States Patent
Donovan et al.

(10) Patent No.: US 9,301,883 B2
(45) Date of Patent: Apr. 5, 2016

(54) FEMININE HYGIENE PRODUCT

(71) Applicants: Rachel Donovan, New York, NY (US);
Heather Han, Brooklyn, NY (US)

(72) Inventors: Rachel Donovan, New York, NY (US);
Heather Han, Brooklyn, NY (US)

(*) Notice: Subject to any disclaimer, the term of this patent is extended or adjusted under 35 U.S.C. 154(b) by 189 days.

(21) Appl. No.: 13/869,004

(22) Filed: Apr. 23, 2013

(65) Prior Publication Data

US 2013/0261588 A1    Oct. 3, 2013

Related U.S. Application Data

(63) Continuation of application No. PCT/US2012/030646, filed on Mar. 27, 2012.

(51) Int. Cl.
*A61F 13/34* (2006.01)
*A61F 13/26* (2006.01)

(52) U.S. Cl.
CPC ................. *A61F 13/34* (2013.01); *A61F 13/26* (2013.01)

(58) Field of Classification Search
CPC ......... A61F 13/02; A61F 13/15; A61F 13/20; A61F 13/26; A61F 13/34
USPC ............................ 604/385.02, 385.17, 385.18
See application file for complete search history.

(56) References Cited

U.S. PATENT DOCUMENTS

| 3,857,395 | A | * | 12/1974 | Johnson et al. | ................. 604/14 |
| 3,913,579 | A | * | 10/1975 | Srinivasan et al. | ............ 604/366 |
| 6,059,763 | A | | 5/2000 | Brown | |
| 6,186,994 | B1 | * | 2/2001 | Bowles et al. | ........... 604/385.17 |
| 2009/0112148 | A1 | | 4/2009 | Morrow | |

FOREIGN PATENT DOCUMENTS

| DE | 9312949 U1 | 6/1994 |
| RU | 2290154 C2 | 12/2006 |
| RU | 2370252 C2 | 10/2009 |

OTHER PUBLICATIONS

International Search Report and Written Opinion for PCT Application No. PCT/US2012/030646, mailed Nov. 22, 2012, 6 pages.
International Preliminary Report on Patentability for PCT Patent Application No. PCT/US2012/030646, mailed on Oct. 9, 2014, 5 pages.

* cited by examiner

*Primary Examiner* — Melanie Hand
(74) *Attorney, Agent, or Firm* — Brake Hughes Bellermann LLP (57) ABSTRACT

A feminine hygiene product including a tampon, an absorbent pad, and a string connecting the tampon to the absorbent pad is disclosed. The string can include at least one breakable section, or the string may releasably affixed to the absorbent pad. The tampon and/or the absorbent pad can be formed from cotton, rayon, or a cotton-rayon mixture. The feminine hygiene product can further include an applicator sized to accommodate the tampon and the absorbent pad, and to facilitate deployment of the same.

13 Claims, 6 Drawing Sheets

FEMININE HYGIENE PRODUCT

CROSS-REFERENCE TO RELATED APPLICATION

This application is a continuation of International Patent Application No. PCT/US2012/030646, filed on Mar. 27, 2012, which is incorporated by reference herein in its entirety.

FIELD OF THE INVENTION

The present invention relates generally to an improved feminine hygiene product comprising an operably connected tampon and absorbent pad.

BACKGROUND OF THE INVENTION

Tampons, and applicators for the deployment thereof, have been known in the art for some time. Most such systems consist of generally cylindrical applicator which houses the tampon and facilitates the deployment into the vaginal canal thereof. Such applicators are typically formed of two coaxial, telescoping pieces, with the inner piece acting as a plunger to force the tampon through the top of the outer piece during deployment. This is generally the extent of known tampon application systems. Improvements to such systems are generally directed to changing the shape, materials, or methods of forming the tampon. However, in use such systems can frequently fail to adequately prevent leakage of bodily fluids and can be otherwise unsanitary and inconvenient. Such unsanitary conditions can lead to toxic shock syndrome and other health complications. In addition, many known tampon products contain harmful chemicals that may lead to cancer or other health complications.

Absorbent pad have also been known in the art for some and generally consist of a rectangular-shaped piece of absorbent material that is placed beneath the undergarment to absorb any bodily fluids during the menstrual cycle. However, like known tampon systems, known pad configurations can frequently fail to adequately absorb leakage of bodily fluids and can be otherwise unsanitary and inconvenient. Pads are also often bulky and can be uncomfortable wear for extended periods of time and are not as convenient to carry in handbag or such.

The inadequacies of known feminine hygiene products can lead to insecurity, embarrassment and frustration for many women, in addition to the resulting costs of replacing and/or cleaning items ruined by the failure of these known products. Thus, there is a need in the art for an improved feminine hygiene product that overcomes the aforementioned shortcomings in the art.

SUMMARY OF THE INVENTION

A feminine hygiene product including a tampon, an absorbent pad, and a string connecting the tampon to the absorbent pad is disclosed. In some embodiments, the string includes at least one breakable section, while in the same or different embodiments the string is releasably affixed to the absorbent pad. The tampon can be formed from at least one of cotton, rayon, or a cotton-rayon mixture, while the absorbent pad can be formed from cotton, rayon, or a cotton-rayon mixture.

In some embodiments, the feminine hygiene product further includes an applicator sized to accommodate the tampon and the absorbent pad, and the applicator does so accommodate the tampon and the absorbent pad. In the same or other embodiments, the applicator includes an outer shell having an opening end and a plunger having a plunger end and an open end, where the opening end of the outer shell includes one or more deflectable members, and where the outer shell and the plunger are telescopically connected such that an application of force of the plunger end causes the deflection of at least one of the deflectable members.

The tampon can be located inside the applicator such that the tampon abuts an inside surface of the opening end, and the absorbent pad can be located inside the applicator such that the absorbent pad abuts an inside surface of the plunger end. The tampon can also be located in a configuration where it further abuts the open end of the plunger such that the application of force to the plunger end of the plunger is transferred to the tampon. The plunger can be cylindrically shaped and the absorbent pad can be rolled into a coaxial cylindrical shape when located therein.

In some embodiments, the feminine hygiene product can further include sealed packaging having at least one tearable portion, where the applicator is located therein.

DETAILED DESCRIPTION OF THE INVENTION

The present invention is directed to an improved feminine hygiene product which includes a tampon and an absorbent pad, operably connected together with a string. In one embodiment the connected tampon and absorbent pad are located inside an applicator such that the vaginal insertion of the applicator and subsequent deployment of the tampon into the vaginal canal facilitates the removal and use of the pad from the applicator.

As described in more detail below, the applicator can be of the generally known variety, e.g., two coaxial, cylindrical, connected pieces, where the narrower, inner cylinder is used as a plunger to press the tampon through a deflectable opening in the top of the wider, outer cylinder. In this regard, a user of the feminine hygiene product disclosed herein can insert the applicator into the vaginal canal and deploy the tampon in a manner most are already familiar with while also facilitating the removal of the absorbent pad from the plunger where it is initially located. This configuration is especially advantageous in that it provides the user with both the tampon and the absorbent pad, and the added protection against leakage such a pad provides, in a single, convenient applicator unit. The absorbent pad can be coated with adhesives and foldable such that it can be folded into a size appropriate for use as a panty liner and can adhere to the undergarment. In addition, the string attaching the tampon and absorbent pad can have a weakened section to facilitate easy breakage of the string and thus to permit the separability of the tampon from the absorbent pad after the deployment thereof. Thus a single, compact product which provides improved protection against leaks is provided.

What follows is a detailed description of the improved feminine hygiene product disclosed herein with reference to the figures and, specifically, with reference to the operable deployment of such product in an embodiment which includes an applicator. It is to be understood that the exact manner in which a potential user deploys the product can differ from that described herein.

Figure 1A:
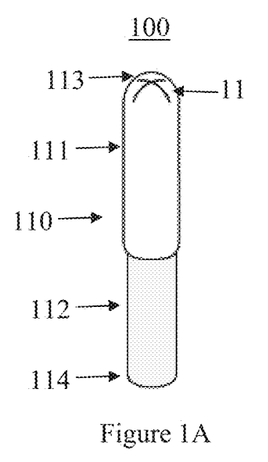
FIG. 1A illustrates an improved feminine hygiene product with an applicator in accordance with an embodiment of the present invention.

FIG. 1A illustrates improved feminine hygiene product 100 according to one embodiment of the present invention. In this embodiment, feminine hygiene product 100 includes an applicator 110 which is composed of outer shell 111 and plunger 112, which are arranged in a telescoping configuration with outer shell 111 being sized such that plunger 112 can be moved further into the cavity of outer shell 111. The outer shell 111 and plunger 112 can be cylindrically shaped, as illustrated in FIG. 1A; however, it is understood that other appropriate shapes can be employed without deviating from the spirit of the invention. Outer shell 111 includes opening end 113, and plunger 112 includes plunger end 114. Opening end 113 has one or more deflectable members 11, and in the embodiment illustrated in FIG. 1A, opening end 113 has four deflectable members 11. However, persons of ordinary skill in the art will understand that opening end 113 can have a different number of deflectable members 11.

Figure 1B:
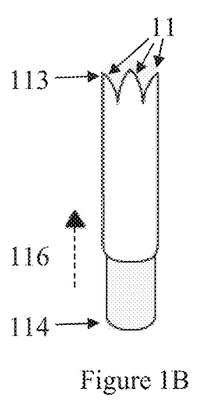
FIGS. 1B-1H illustrate the features and configuration of an improved feminine hygiene product with an applicator over the course of a deployment of the same in accordance with an embodiment of the present invention.
Figure 1C:
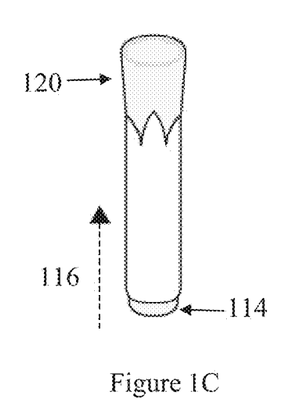

FIG. 1B through FIG. 1H illustrate the deployment for use of improved feminine hygiene product 100 in accordance with an embodiment of the present invention. As illustrated in FIG. 1B, improved feminine hygiene product 100 is configured such that it can be deployed from applicator 110 by the application of a force to plunger end 114 which causes plunger 112 to move further into outer shell 111 in a telescoping fashion. In FIGS. 1B and 1C, dashed arrow 116 illustrates the direction of telescopic movement cause by the application of force to plunger end 114. It is understood that, generally, in practice a user will insert opening end 113 into the vaginal canal to the appropriate depth before depressing plunger 112 to deploy tampon 120 into the canal.

Figure 1D:
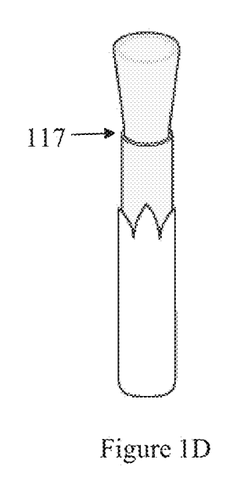

As illustrated in FIG. 1B, applicator 110 is configured such that the application of force to plunger end 114 and the resulting telescopic motion of plunger 112 causes the outward deflection of deflecting members 11, thereby creating an opening in opening end 113. In one embodiment, as illustrated in FIG. 1D, tampon 120 is located partially inside and abutting open end 117 of plunger 112. In this embodiment tampon 120 further abuts the inside surface of opening end 113 such that the application of force to plunger end 114 is transferred to the inside surface of opening end 113 via tampon 120, thereby allowing for the deflection of deflecting members 11 upon the application of such force, as illustrated in FIG. 1C. Persons of ordinary skill in the art will understand that in some embodiments tampon 120 can be located away from the inside surface of opening end 113 when product 100 is in its undeployed configuration (illustrated in FIG. 1A) and then move to a position abutting the inside surface of opening end 113 after three is applied to plunger end 114 causing plunger 112 to move telescopically in direction 116. Persons of ordinary skill in the art will further understand that in other embodiments improved feminine hygiene product 100 can be configured such that open end 117 of plunger 112 directly contacts the inside surface of opening end 113 of outer shell 111 upon the application of force to plunger end 114 in direction 116. In such other embodiments, tampon 120 can be initially located further inside plunger 112, and/or can be of a different shape than the conical shape depicted in FIG. 1D.

Figure 1E:
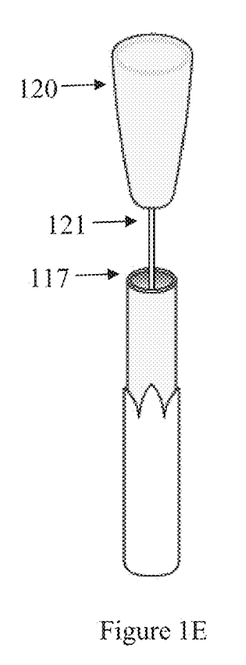
Figure 1F:
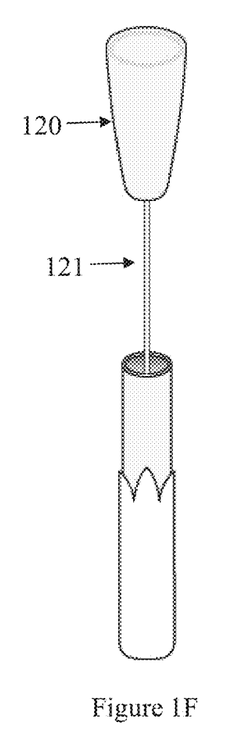

In one embodiment, as illustrated in FIG. 1E, tampon 120 is connected to one end of string 121. In this embodiment, improved feminine hygiene product 100 is configured to be removed from applicator 110 by pulling tampon 120 out of plunger 112, which will pull connected string 121 out of its initial location in plunger 112. It is understood that, generally, in practice a user will insert opening end 113 into the vaginal canal prior to depressing plunger 112 such that in practice the user will pull applicator 110 away from the body while friction between the vaginal walls and tampon 120 will hold tampon 120 in place. Product 100 is configured such that a user can perform this retrieval action when, for example, applicator 110 is in the deployment stage illustrated in FIG. 1D, though persons of skill in the art will understand that such a removal action could be performed in an earlier stage of deployment, for example the stage depicted in FIG. 1C. FIG. 1F illustrates the further removal of string 121, which, as described below, is connected to absorbent pad 130, which in the embodiment illustrated in FIG. 1F, is still located within plunger 112.

Figure 1G:
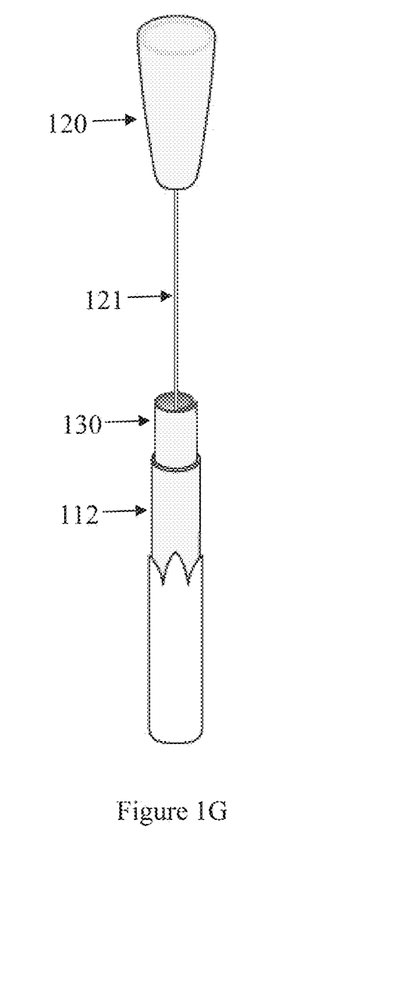
Figure 1H:
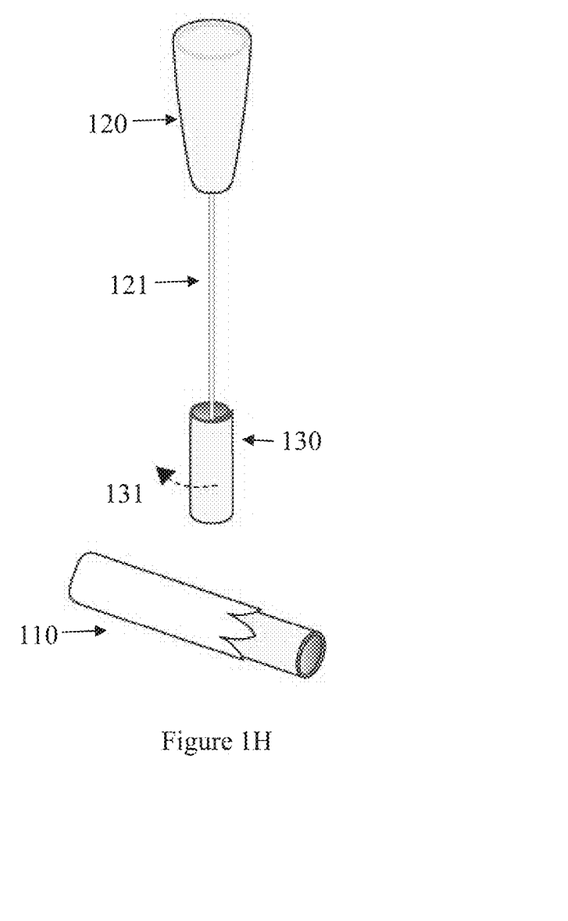

FIG. 1G illustrates the further deployment of product 100, showing tampon 120, connected to absorbent pad 130 by string 121. As discussed above, in this embodiment the product 100 is configured such that the action of pulling tampon 120 out of plunger 112 (or by pulling applicator 110 away from the body while tampon 120 remains in place) causes absorbent pad 130 to also be pulled out of plunger 112 by virtue of its connection to tampon 120 by string 121. As illustrated in FIG. 1G, absorbent pad 130 is initially positioned inside plunger 112 in a rolled configuration, though persons of skill in the art will understand that other configurations, such as a folded configuration, are possible. In some embodiments, absorbent pad 130 can further be initially positioned inside plunger 112 such that it abuts the inside surface of plunger end 114 before the deployment of product 100. FIG. 1H illustrates the deployment of product 100, whereby it has been fully removed from applicator 110. As illustrated in FIG. 1H, absorbent pad 130 is configured such that it can be unrolled by a user in the direction of dashed arrow 131. Empty applicator 110, which is ready for disposal at this stage of deployment, is also illustrated in FIG. 1H.

Figure 2A:
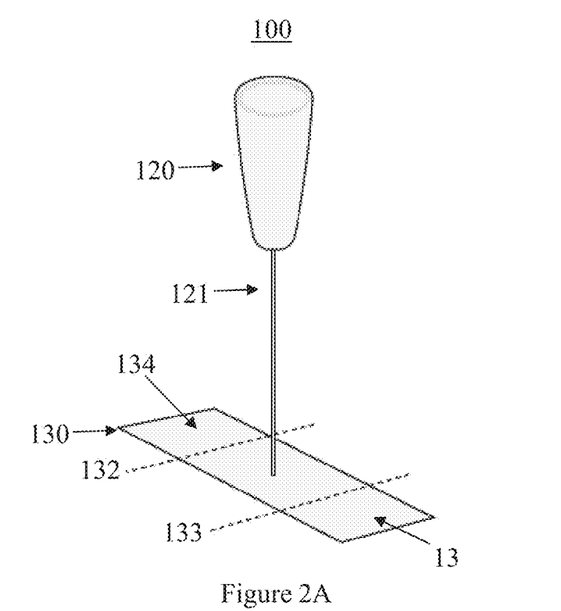
FIG. 2A illustrates a top perspective view of an improved feminine hygiene product in accordance with an embodiment of the present invention.
Figure 2B:
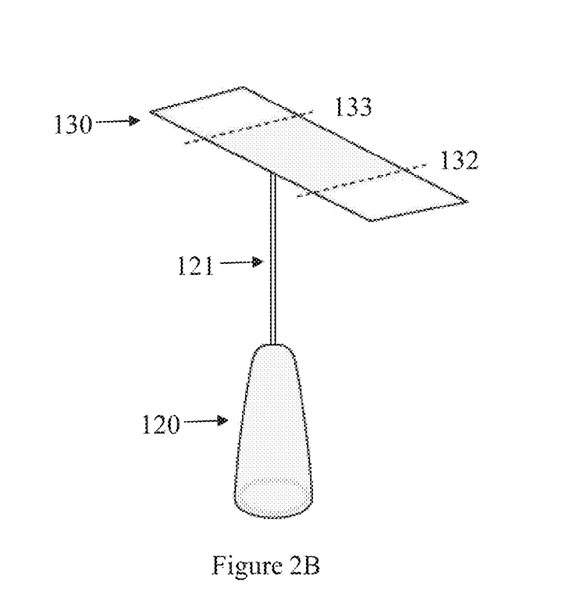
FIG. 2B illustrates a bottom perspective view of an improved feminine hygiene product in accordance with an embodiment of the present invention.

FIG. 2A illustrates a top perspective view of improved feminine hygiene product 100, showing conical shaped tampon 120 connected to absorbent pad 130 via string 121. In one embodiment absorbent pad 130 can have foldable portions 132, 133 as indicated by dashed lines 132, 133 illustrated in FIG. 2A. Foldable portions 132, 133 can be creases in absorbent pad 130 formed during the manufacturing process of the pad. As illustrated in FIG. 2A, absorbent pad 130 can be rectangular in shape, though persons of ordinary skill in the art will understand that other shapes are possible, such as shapes having curved sides, among others. FIG. 2B illustrates a bottom perspective view of the improved feminine hygiene product 100 illustrated in FIG. 2A.

Figure 2C:
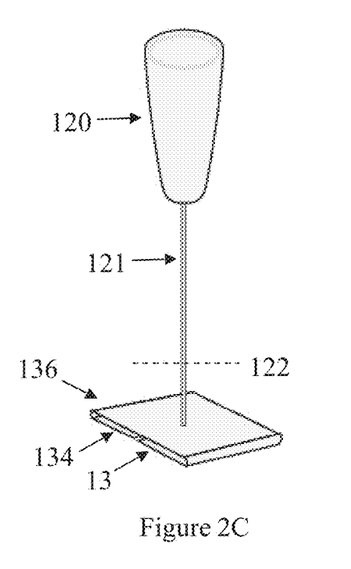
FIGS. 2C-2D illustrate perspective views of an improved feminine hygiene product in accordance with an embodiment of the present invention.

In some embodiments, the feminine hygiene product 100 of FIG. 2A can have a layer of adhesive on one or more portions of adsorbent pad 130. In one embodiment, a layer of adhesive material is placed over the portions of the top of absorbent pad 130 outside of foldable creases 132, 133, designated in FIG. 2A as areas 134, 13, respectively. In the same or another embodiment, a layer of adhesive material is placed over the entire surface of the bottom of absorbent pad 130, shown in FIG. 2B. In such embodiments, absorbent pad 130 is configured such that areas 134, 13 can be folded downward and over along foldable creases 132, 133 such that those areas become bottom of a folded absorbent pad 136, as illustrated in FIG. 2C. In those embodiments where a layer of adhesive material is placed over areas 134, 13, the bottom of folded absorbent pad 136 will have that layer of adhesive material, thereby allowing a user of product 100 to adhere folded absorbent pad 136 to her undergarment.

Figure 2D:
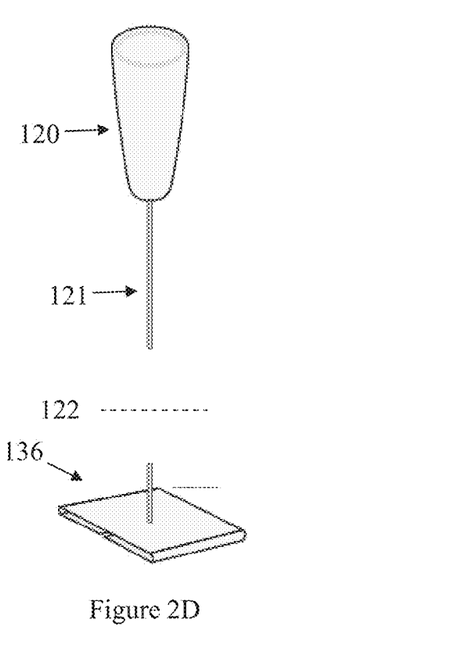

FIG. 2C further illustrates string 121 having breakable section 122, as shown by dashed line 122. Breakable section 122 can be a weakened portion of string 121 formed during the manufacturing process, such as a scoring of the string material. As illustrated in FIG. 2D, improved feminine hygiene product 100 is configured such that string 121 can be broken along breakable section 122, thereby separating folded absorbent pad 136 from tampon 120 and facilitating the ease of use of both elements. In other embodiments, string 121 is releasably affixed to absorbent pad 130, such that it can be detached from absorbent pad 130.

Figure 3:
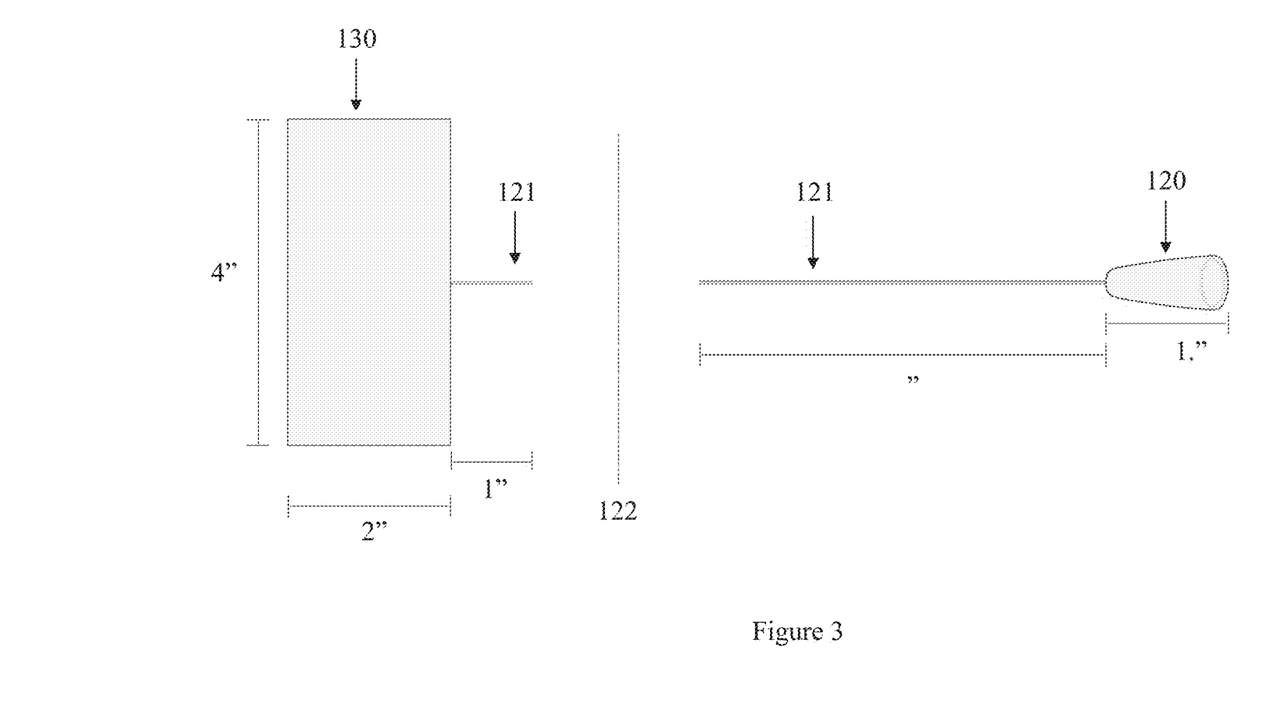
FIG. 3 illustrates a schematic view of an improved feminine hygiene product in accordance with an embodiment of the present invention.

FIG. 3 illustrates a schematic view of improved feminine hygiene product 100 showing exemplary dimensions of the product in one embodiment. As illustrated in FIG. 3, absorbent pad 130 can be 4 inches long by 2 inches wide, string 121 can be 6 inches long with breakable section 122 located 1 inch away from absorbent pad 130 and the remaining 5 inches attached to tampon 120, and tampon 120 can be 1.5 inches long and conically shaped. Persons of ordinary skill in the art will understand that these dimensions are exemplary and other, larger or small dimension, are possible. For example, absorbent pad 130 can be 4 to 7 inches long by 1.5 to 4 inches wide, string 121 can be 5 to 7 inches long with breakable portion 121 located 1 to 3 inches away from absorbent pad 130, and tampon 120 can be 1.25 to 2.5 inches long. Persons of skill in the art will further appreciate that the shape of tampon 120 and/or the shape of absorbent pad 130 can differ from the examples provided herein. For example, tampon 120 can be cylindrical or funnel-shaped, and absorbent pad 130 can have in-cut sides, wings, be folded or bendable.

In accordance with some embodiments of the present invention, tampon 120 can be formed from cotton, rayon or a mixture of both. Further, in the same or other embodiments, absorbent pad 130 can be formed from cotton, rayon or a mixture of both. In some embodiments, tampon 120 and/or absorbent pad 130 can be formed from organic cotton, and in yet other embodiments, tampon 120 and absorbent pad 130 can be formed to be chlorine free, fragrance free, and/or hypoallergenic. Tampon 120 can also be formed from organic cotton of a weight of 6 gm or under, to achieve a lighter absorbency tampon, and from organic cotton of a weight of 6 to 9 gm, to achieve a higher absorbency tampon. Absorbent pad 130 can be formed from plastic, as is known in the art.

Figure 4:
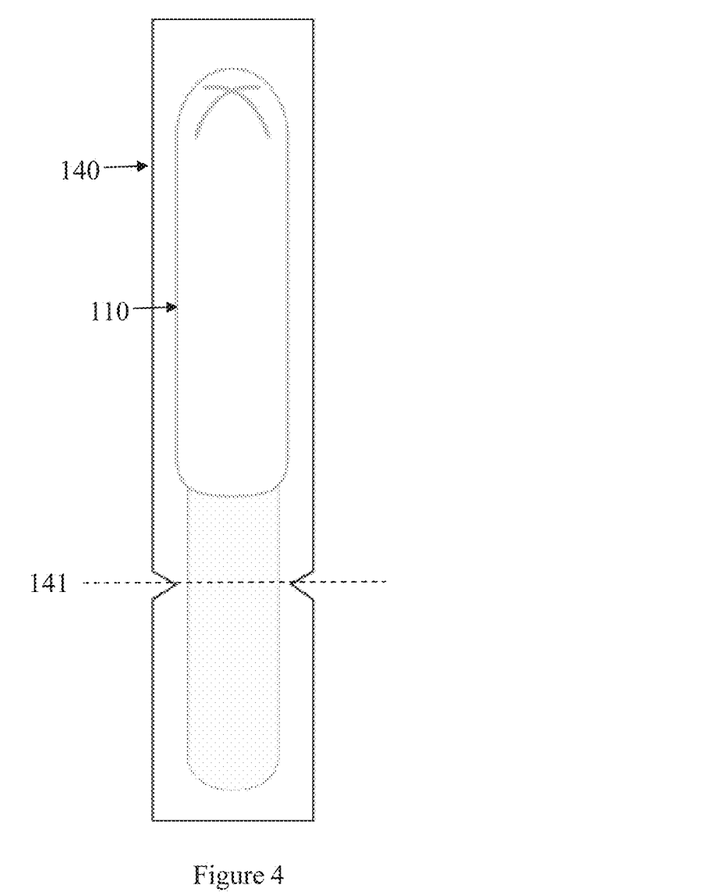
FIG. 4 illustrates a sealed packaging for an improved feminine hygiene product with an applicator in accordance with an embodiment of the present invention.

In accordance with one embodiment of the present invention, FIG. 4 illustrates sealed packaging 140 having applicator 110, and thereby product 100, sealed therein. As illustrated sealed packaging 140 has at least on tearable portion 141, as indicated in FIG. 4 by dashed line 141, to facilitate ease of removal of applicator 110 and improved feminine hygiene product 100 therein. In some embodiments, sealed packaging 140 is formed from a light paper material, though persons of ordinary skill in the art will understand that other material, such as thin plastics, can also be used to form sealed packaging 140. In some embodiments, sealed packaging 140 can be color coded to indicate the properties of the product 100 contained therein. For example, a darker shade of packaging 140 can indicate that the product 100 contained therein is designed for heavy-flow days, whilst a lighter shade of packaging 140 can indicate that the product 100 contained therein is designed for light-flow days.

It will be understood that the foregoing is only illustrative of the principles described herein, and that various modifications can be made by those skill in the art without departing form the scope and spirit of the invention. Moreover, features of embodiments described herein may be combined and/or rearranged to create new embodiments.

What is claimed is:

1. A feminine hygiene product, comprising: a folded or rolled absorbent pad, the absorbent pad being folded or rolled in a cylindrical shape; a tampon separate from and external to the folded or rolled absorbent pad; a string connecting the tampon to a distal outer longitudinal edge of the folded or rolled absorbent pad; and an applicator, wherein the applicator is sized to enclose the tampon and the folded or rolled absorbent pad and does so enclose; wherein the applicator comprises: an outer shell having an opening end, and a plunger having a plunger end and an open end, wherein the opening end comprises one or more deflectable members, and wherein the outer shell and the plunger are telescopically connected such that an application of force on the plunger end causes the deflection of at least one of the one or more deflectable members; and wherein the folded or rolled absorbent pad is located inside the applicator such that the folded or rolled absorbent pad abuts an inside surface of the plunger end.

2. A feminine hygiene product, comprising: a tampon; an absorbent pad; a string connecting the tampon to the absorbent pad; and an applicator sized to accommodate the tampon and the absorbent pad, the applicator including an outer shell and a plunger, the outer shell having an opening end and a distal end, the plunger having a plunger end and an open end, the opening end of the outer shell having one or more deflectable members, wherein the outer shell and the plunger are telescopically arranged so that an application of force on the plunger end causes deflection of at least one of the one or more deflectable members of the opening end of the outer shell; and wherein the tampon is disposed inside the applicator such that the tampon abuts an inside surface of the opening end of the outer shell.

3. The feminine hygiene product of claim 2, wherein the tampon further abuts the open end of the plunger such that the application of force to the plunger end of the plunger is transferred to the tampon.

4. The feminine hygiene product of claim 1, wherein the plunger is cylindrically shaped and wherein the folded or rolled absorbent pad is rolled into a coaxial cylindrical shape.

5. The feminine hygiene product of claim 1, further comprising:
sealed packaging having at least one tearable portion, wherein the tampon and the folded or rolled absorbent pad attached thereto are located in the sealed packaging.

6. The feminine hygiene product of claim 1, further comprising:
sealed packaging having at least one tearable portion, wherein the applicator is located in the sealed packaging.

7. The feminine hygiene product of claim 2, wherein the absorbent pad is rolled or folded and disposed inside the applicator such that the rolled or folded absorbent pad abuts an inside surface of the plunger end.

8. The feminine hygiene product of claim 2, wherein the plunger has a tubular structure.

9. The feminine hygiene product of claim 8, wherein the plunger end includes an open end of the tubular structure of the plunger.

10. The feminine hygiene product of claim 2, wherein the distal end of outer shell has an opening though which the plunger is telescopically connected to the outer shell.

11. The feminine hygiene product of claim 2, wherein the string comprises at least one breakable section.

12. The feminine hygiene product of claim 2, wherein the string is releasably affixed to the absorbent pad.

13. The feminine hygiene product of claim 2, wherein the tampon and the absorbent pad are formed from at least one of cotton, rayon, or a cotton-rayon mixture.

* * * * *